(12) United States Patent
Schlegel et al.

(10) Patent No.: US 6,711,237 B1
(45) Date of Patent: Mar. 23, 2004

(54) CONTOUR COLLIMATOR FOR USE IN RADIOTHERAPY

(75) Inventors: Wolfgang Schlegel, Heidelberg (DE); Otto Pastyr, Leimen (DE); Gernot Echner, Wiesenbach (DE); Karl-Heinz Hover, Sinsheim (DE); Jurgen Richter, Würzburg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/890,840
(22) PCT Filed: Feb. 7, 2000
(86) PCT No.: PCT/DE00/00347
§ 371 (c)(1), (2), (4) Date: Jan. 16, 2002
(87) PCT Pub. No.: WO00/46813
PCT Pub. Date: Aug. 10, 2000

(30) Foreign Application Priority Data

Feb. 6, 1999 (DE) .......................... 199 04 972

(51) Int. Cl.[7] ................................ G21K 1/04
(52) U.S. Cl. ...................... 378/152; 378/150
(58) Field of Search .................... 378/64, 65, 145, 378/147, 148, 150, 151, 152, 153

(56) References Cited

U.S. PATENT DOCUMENTS

| | | | | |
|---|---|---|---|---|
| 3,736,486 A | * | 5/1973 | Gould et al. | 318/624 |
| 4,672,652 A | * | 6/1987 | Hüttenrauch et al. | 378/152 |
| 4,739,173 A | * | 4/1988 | Blosser et al. | 250/505.1 |
| 4,794,629 A | * | 12/1988 | Pastyr et al. | 378/152 |
| 4,987,309 A | * | 1/1991 | Klasen et al. | 250/492.1 |
| 5,012,506 A | * | 4/1991 | Span et al. | 378/152 |
| 5,351,280 A | * | 9/1994 | Swerdloff et al. | 378/65 |
| 5,442,675 A | * | 8/1995 | Swerdloff et al. | 378/65 |
| 5,555,283 A | * | 9/1996 | Shiu et al. | 378/151 |
| 6,188,748 B1 | * | 2/2001 | Pastyr et al. | 378/151 |

* cited by examiner

*Primary Examiner*—Allen C. Ho
(74) *Attorney, Agent, or Firm*—Steven J. Hultquist; Marianne Fuierer

(57) ABSTRACT

A contour collimator for radiation therapy has a plurality of diaphragm elements that are movable with respect to each other by means of drive units. The diaphragm elements of the invention are supported only on the side near the drive units for ease of movement. This allows larger contour collimators to be constructed having relatively heavy diaphragm elements while retaining relatively small motors.

12 Claims, 8 Drawing Sheets

CONTOUR COLLIMATOR FOR USE IN RADIOTHERAPY

CROSS REFERENCE TO RELATED APPLICATIONS

Figure 1:
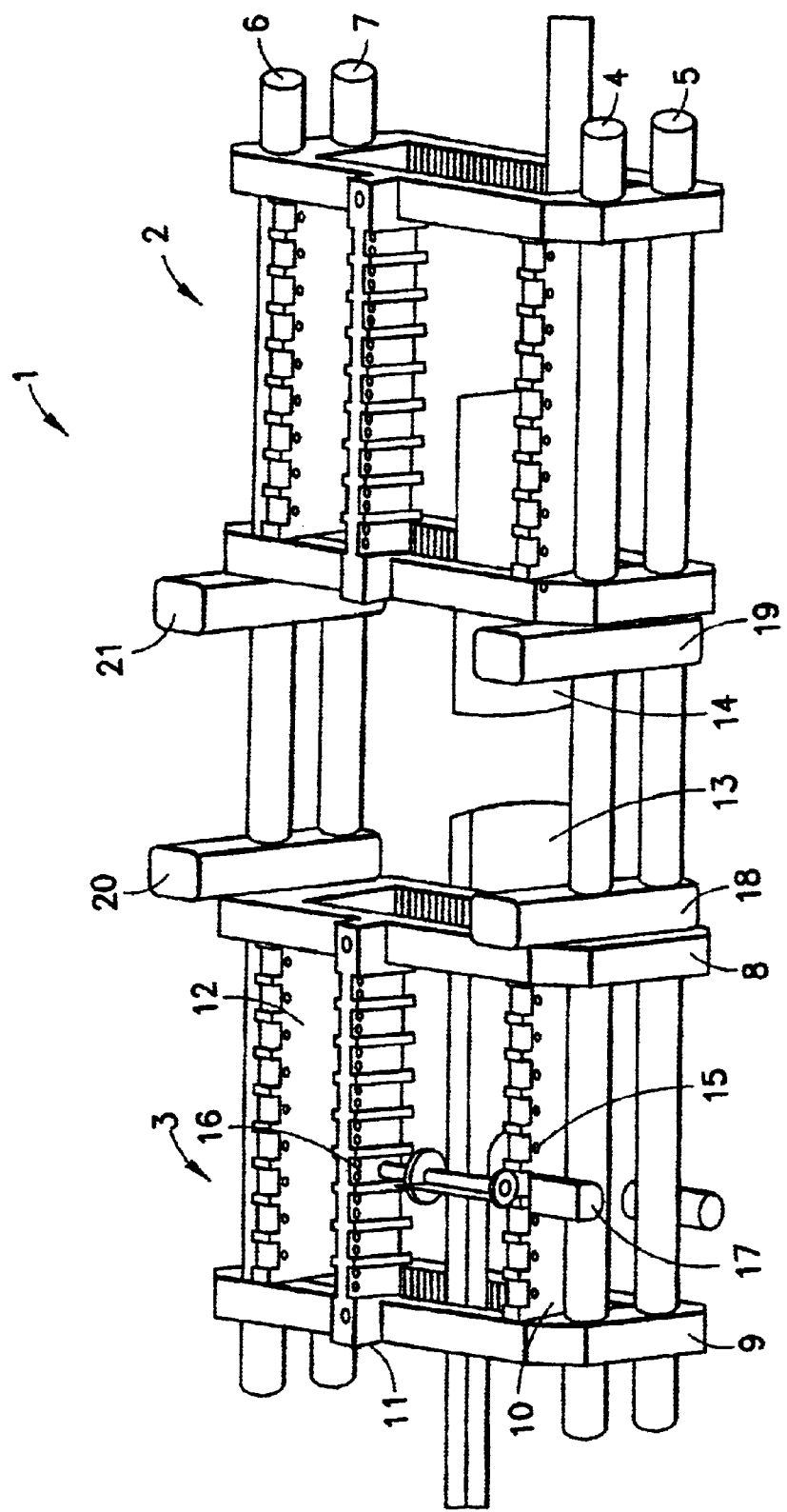

This application is filed under the provisions of 35 U.S.C. §371 and claims the priority of International Patent Application No. PCT/DE00/00347 filed Feb. 7, 2000, which in turn claims priority of German Patent Application No. 199 04 972.6 filed on Feb. 6, 1999.

The invention relates to a contour collimator for radiation therapy having a plurality of diaphragm elements arranged movably with respect to each other, such movement being powered by a drive unit.

A contour collimator of this kind is known for example from DE 195 36 804.5 A1. In the contour collimator described therein, a drive unit is provided for each of the plurality of diaphragm elements, and the drive units move the diaphragm elements in two directions along a guide rail. By means of the control for each individual diaphragm element, a radiation field is set up with which it is possible to create a special contour for radiation on the body part that is being radiated. This contour collimator is especially suitable for small radiation fields. It is impossible to increase the size of this known contour collimator in order to create larger radiation fields because the motors such an increase in size would necessitate are too big and they can scarcely be arranged about the radiation field.

The task of the present invention was therefore to adapt a known contour collimator in such a way that it is also suited for use with larger radiation fields.

This task has been solved by supporting the diaphragm elements only on the side of the drive unit.

The invention is based on the premise that the diaphragm elements must be both supported and movable. In the known contour collimator, this facility is provided in the form of a rail that supports the weight of the diaphragm elements and guides them in courses parallel to one another.

However, particularly when larger diaphragm elements are used, a high degree of friction is generated in the guide rails, the diaphragm elements tend to jam, and they cannot be moved without the application of much power. The use of larger motors leads to increased size of the contour collimator, an undesirable and unacceptable increase in weight and, most importantly, to space problems since the motors should be arranged as closely as possible to the diaphragm elements.

However, the diaphragm elements of the contour collimator according to the invention are preferably only supported in the area of the drive unit by means of a fixed bearing. The additional guides that are necessary for the diaphragm elements are for positioning purposes only and do not support any of the elements' weight. Jamming is prevented by the proximity of the support to the drive unit, and lower forces are required to move the diaphragm elements. Consequently, the motors can be smaller and can be arranged beside one another in very limited space.

One particularly advantageous embodiment provides for a toothed rack on the diaphragm elements in the area of the drive unit. This toothed rack allows, for example, allows it to operate in conjunction with a gearwheel driven perpendicularly to the direction of movement of the diaphragms, thus achieving a transmission of power with minimal loss. The toothed rack also contributes to a highly compact construction of the contour collimator, since it allows the drive units to be arranged very closely together.

It is further advantageous if a guide for the diaphragm elements is also arranged in direct proximity to the drive unit. The guide in the area of the drive unit ensures reliable cooperation between drive unit and diaphragm element, and particularly when toothed rack and gearwheel cooperate, the guide ensures that the elements remain securely positioned relative to each other.

In order to ensure that the movement of the diaphragm elements generates as little friction as possible, it is proposed to provide a loose bedding for the diaphragm elements on the side of the elements that faces the drive unit. This loose bedding absorbs only minimal lateral weight in a plane perpendicular to the direction of movement of the diaphragms and its primary function is to ensure that the diaphragm elements are guided essentially parallel to each other.

In a preferred configuration, at least two diaphragm elements are arranged with some separation, opposite and slightly offset relative one another, and movably towards one another in more than half the distance of separation. This arrangement provides the capability of "over travel", which allows the formation of special contours and the interlacing of oppositely arranged diaphragm elements.

In order to adjust the contour collimator optimally to the beam path of the radiation beam, it is proposed that the longitudinal axes of at least two diaphragm elements form an angle in their extent from the drive units to their facing sides. In this way, the diaphragm elements can be constructed conically and arranged in a fan formation, with the fan broadening in the direction of the beams being used.

It is advantageous if at least two diaphragm elements have the same length in their extent from the drive units to their facing sites. Indeed, all diaphragm elements preferably have essentially the same shape, in order to reduce the costs of manufacturing the diaphragm elements and to facilitate replacement of faulty diaphragm elements.

A significant reduction in the weight of the diaphragm elements can be achieved if the side of the diaphragm element in the area of the drive units in the direction of movement of the diaphragm elements is longer than its opposite side. Whereas the drive unit cooperates with the diaphragm element on its longer side, the diaphragm element only reaches its full height in the area in which it comes into contact with the radiation.

The collimator can be adjusted rapidly to the most varied operating requirements if at least two and preferably half of the diaphragm elements form a diaphragm group, which is disposed movably in the direction of movement of the diaphragm elements in addition to the movement of the individual diaphragm elements. In this way, the diaphragm group can be simply displaced as a whole, thereby enabling the radiation field to be rapidly enlarged or reduced.

This is preferably achieved by arranging two diaphragm groups opposite one another in the direction of movement of the diaphragms and movably towards one another on guide rails. For example, the contour collimator can then be operated with a high degree of overtravel with closely adjacent diaphragm groups. On the other hand, diaphragm groups having a large separation distance allow the formation of a particularly large and contoured radiated area.

A highly compact configuration of the contour collimator can be achieved if the drive unit is equipped with an axle disposed perpendicularly to the diaphragm element and connected to a motor. In this way, it is possible to provide many closely arranged motors to drive many diaphragm elements. Not only does this result in a particularly compact configuration, but the closely arranged motors can also be controlled easily, and are easily replaced in case of damage.

The design according to the invention particularly allows one drive unit to be assigned to each diaphragm element, so that it is possible to configure the position of the diaphragm elements on an individual basis.

In order to transfer the position of the diaphragm elements to a data processing system for purposes of monitoring and documentation, it is proposed that each drive unit be equipped with a rotary potentiometer, attached with minimal space requirement, or with a linear potentiometer arranged parallel to the diaphragm elements, or with other measuring systems such as inductive or optical systems.

Figure 2:
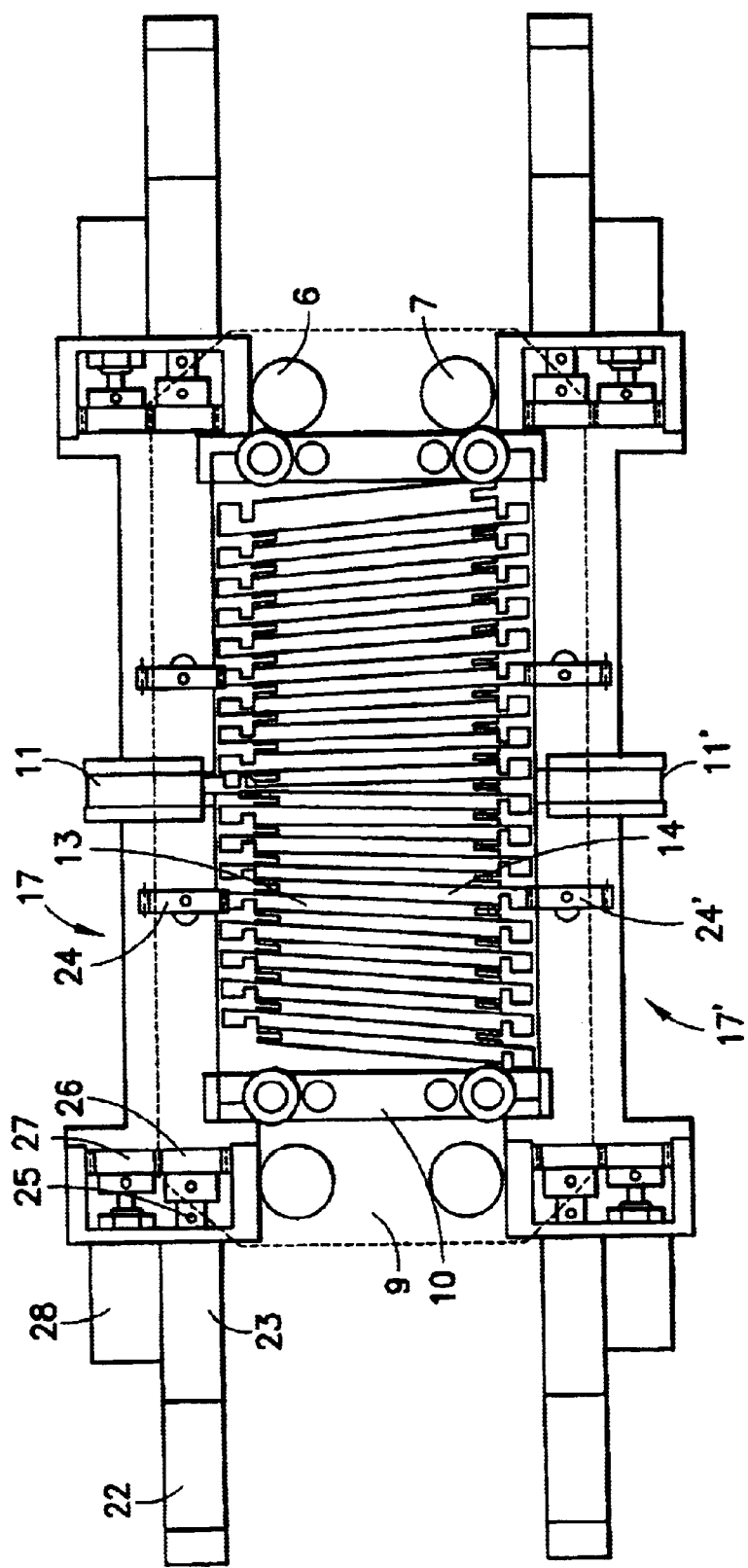
Figure 3:
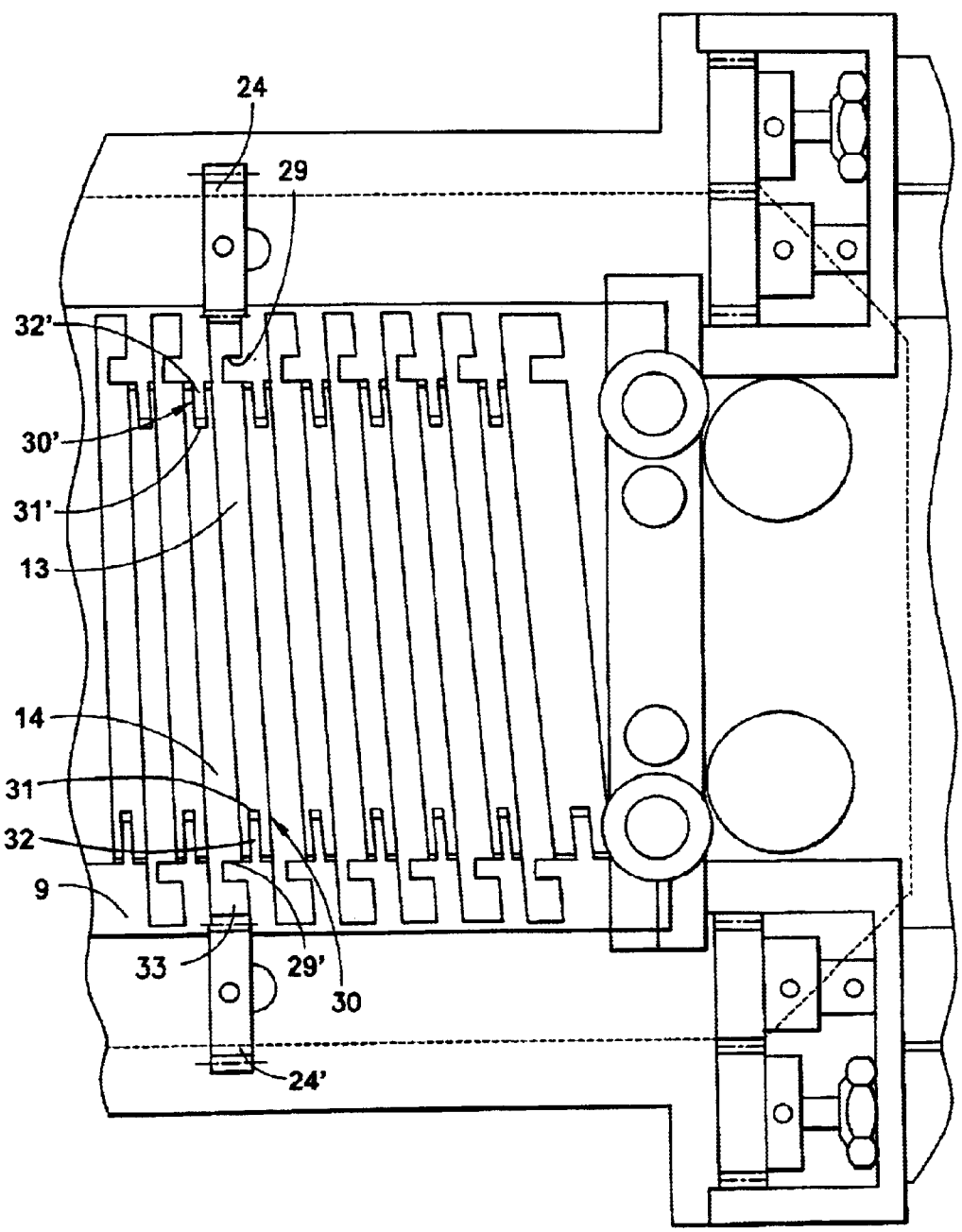
Figure 4:
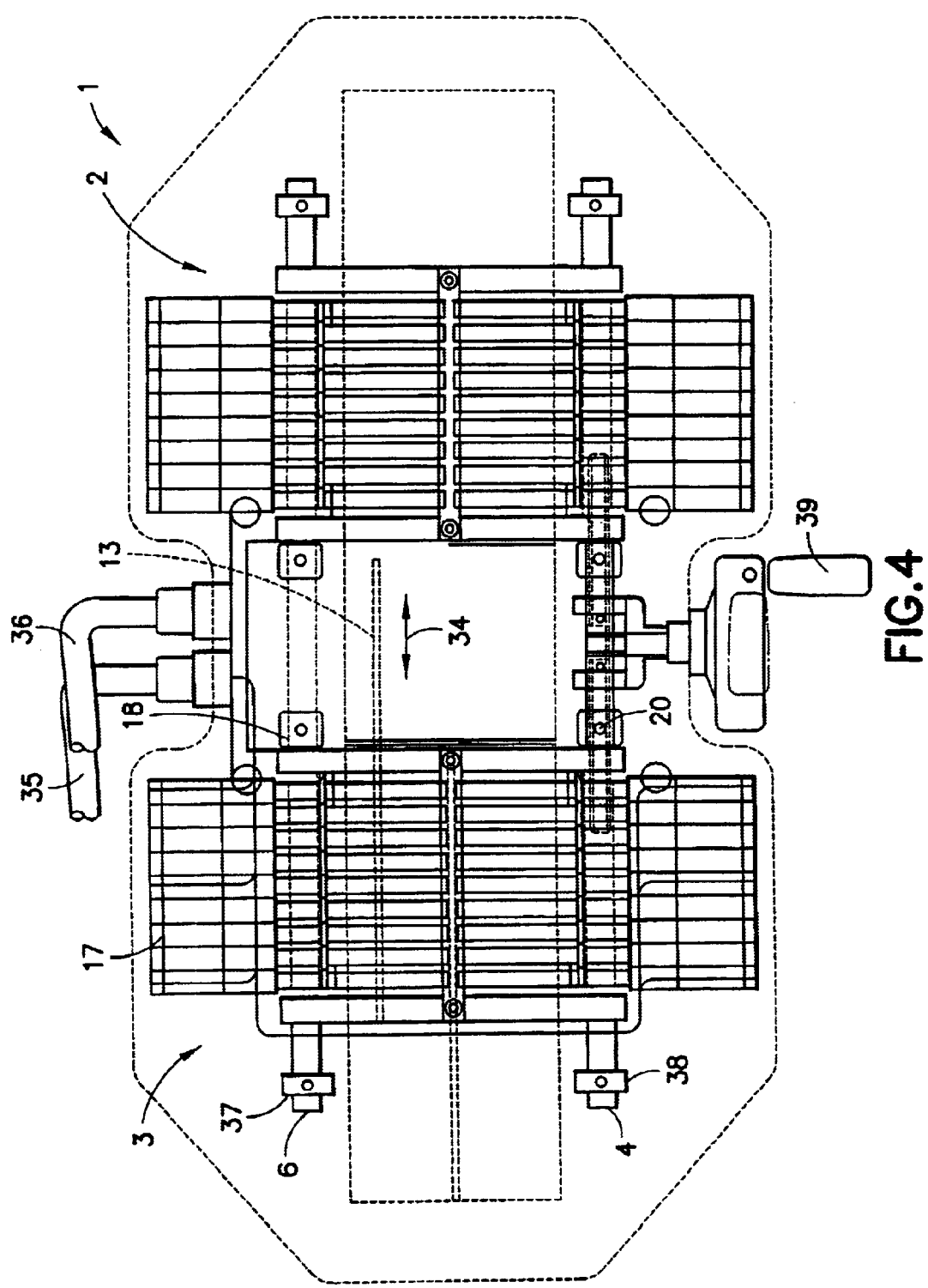
Figure 5:
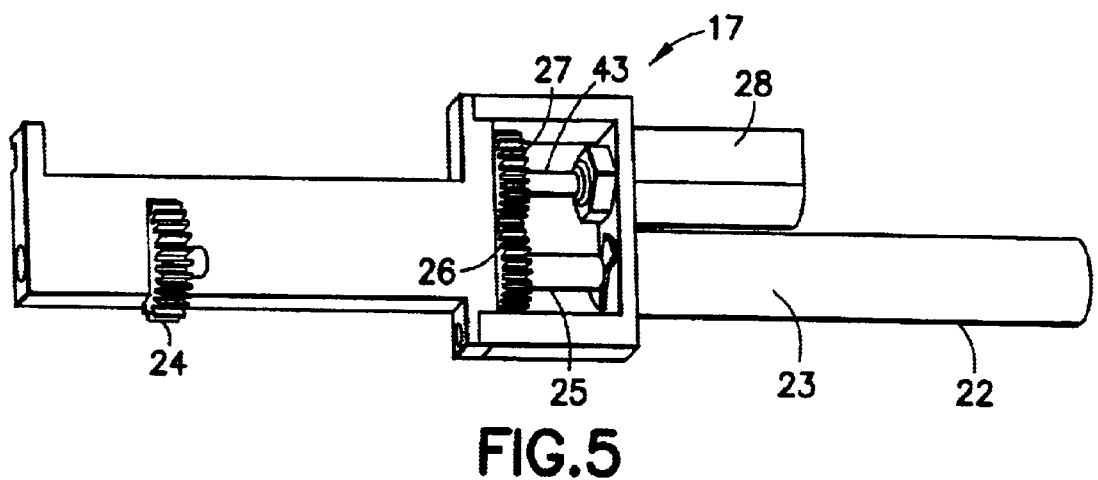
Figure 6:
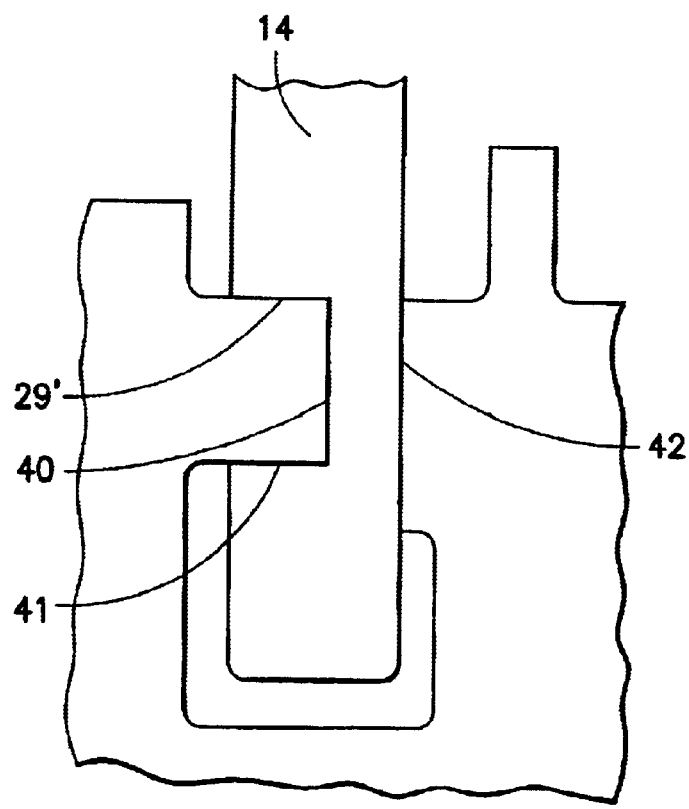
Figure 7:
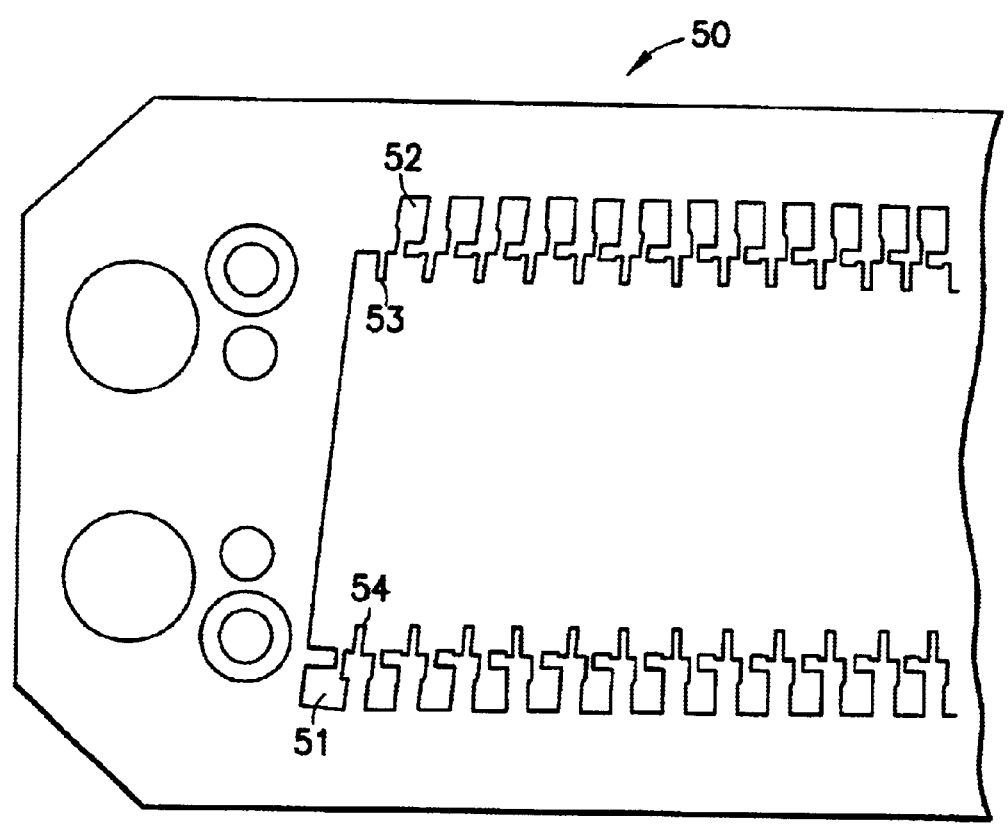
Figure 8:
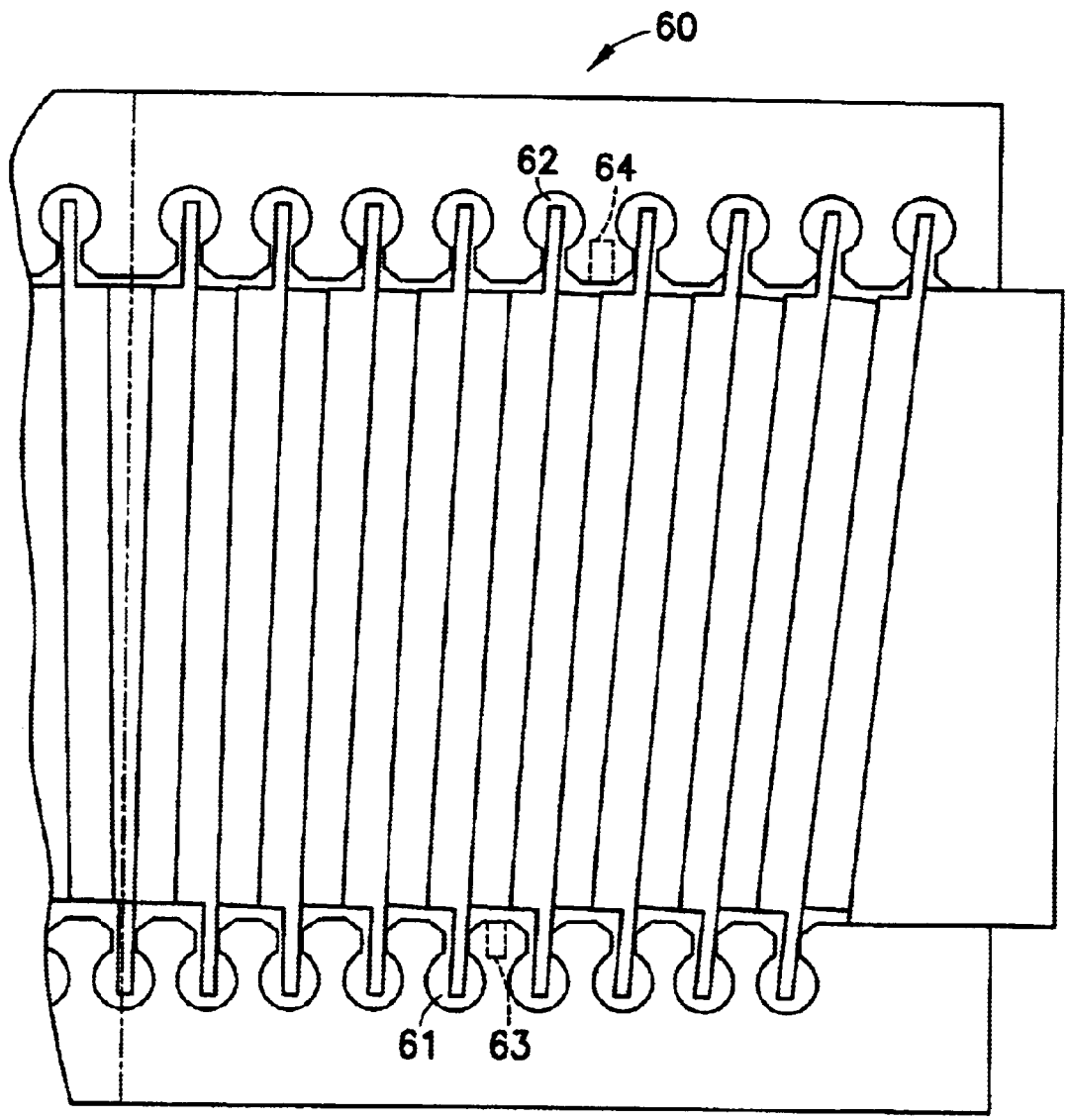
Figure 9:
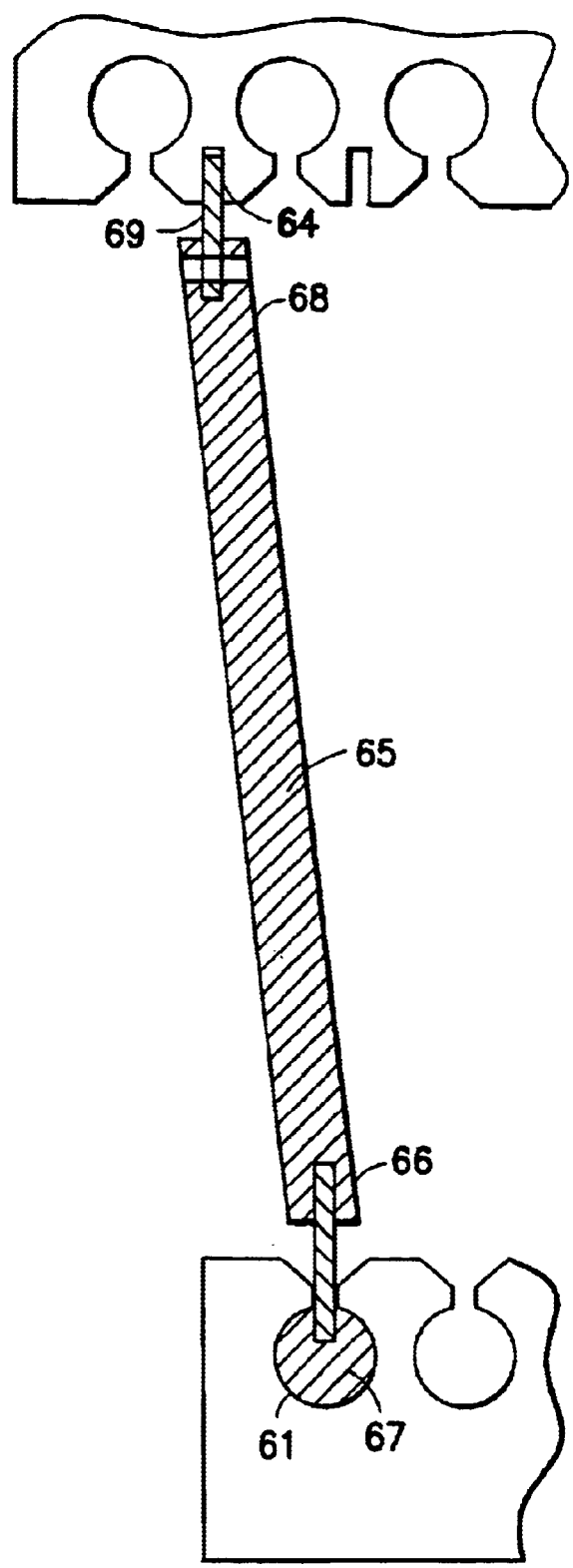

A preferred embodiment of a contour collimator according to the invention is illustrated in the drawing and will be described in detail with reference to the following figures, wherein: FIG. 1 is a three-dimensional view of the contour collimator, diaphragm elements included for exemplary purposes, FIG. 2 is a schematic view of the contour collimator of FIG. 1, seen from the front, FIG. 3 is an enlarged section of FIG. 2, FIG. 4 is a schematic top view of the contour collimator of FIG. 1, FIG. 5 is a view of a drive unit and FIG. 6 is an enlarged detail of FIG. 3, FIG. 7 is a guide plate for the diaphragm elements, FIG. 8 is an alternative embodiment of a guide plate with diaphragm elements attached, and FIG. 9 is an enlarged section of FIG. 8 showing only one diaphragm element.

The contour collimator 1 illustrated in FIG. 1 consists of one right-disposed lamella set 2 and one left-disposed lamella set 3, that are arranged movably with respect to one another on four bracing members 4, 5, 6, 7.

Each set of lamella includes a front plate 8 and a rear plate 9 which are kept at distance from one another by duct spacers 10, 11, 12. The plates are equipped with devices for supporting and guiding lamella members 13, 14. Duct spacers 10, 11, 12 are arranged perpendicularly to the plates and have boreholes 15 and grooves 16 for securing drive units 17 to the lamella set.

Bracing members 4 to 7 supporting lamella sets 2, 3 are attached to bored rods 18, 19, 20, 21, and these rods serve to urge the entire contour collimator 1 towards a plate that is movably attached to a radiation device, which is not illustrated.

For ease of understanding, only one hanging 13 and one standing 14 diaphragm element are shown in FIG. 1, with one drive unit 17. However, the contour collimator is equipped with a multiplicity of diaphragm elements arranged parallel to each other, each of which is connected to its own drive unit 17.

The arrangement of multiple diaphragm elements can be seen in FIG. 2, in which all diaphragm elements are illustrated.

The diaphragm elements are arranged in a slightly semicircular configuration and to save space every second element is driven from above, while those between are driven from below.

For driving the diaphragm elements, one drive unit 17 is provided to drive each element 13. This drive unit consists of a motor 22, a linkage 23 and a driving gearwheel 24. Linkage 23 and gearwheel 24 are connected by a shaft 25, on which gearwheel 26 is arranged to cooperate with a gearwheel 27 and displaces a rotary potentiometer 28 in correspondence with the position of lamella 13. The adjacent diaphragm element 14 is driven by a driving gearwheel 24', which is disposed below it and is equipped with a corresponding drive unit 17'. Drive units 17 and 17' are secured to spacers 10 and 11, 11', and these spacers are in turn attached to bracing members 4 to 7 by means of plates 8 and 9.

The suspension of a diaphragm element is illustrated more clearly in FIG. 3. The entire weight of diaphragm element 13 rests on bearing surface 29, which is arranged directly opposite drive wheel 24. The remaining areas of plate 9 that contact diaphragm element 13 serve solely for guidance, to ensure that diaphragm element 13 does not slip off of bearing surface 29. However, the guidance surfaces formed between diaphragm element 13 and plate 9 cooperate with a loose bedding 30 on the facing plate extremity. A groove 31 is milled into diaphragm element 13 to engage with this loose bedding 30, which receives a retaining pin 32 on plate 9.

The adjacent diaphragm element 14 has a bearing surface 29' that is arranged facing drive gearwheel 24' and supports the weight of the plate. Diaphragm element 14 is seated correspondingly in a loose bedding 30' facing drive gearwheel 24'.

When, for example, drive gearwheel 24 is driven over the toothed rack 33, diaphragm element 13 is shifted. To reduce friction to a minimum, diaphragm element 13 slides over bearing surface 29 and is also guided, by oppositely positioned loose bedding 30. Correspondingly, diaphragm element 14 does not rest on drive gearwheel 24', but on bearing surface 29', while spatial guidance is the function of loose bedding 30'.

The schematic top view of contour collimator 1 view shown in FIG. 4 shows diaphragm element 13 only for the purpose of indicating its movable arrangement in the direction of arrow 34. Diaphragm element 13 is driven by drive unit 17, which—like the other drive units—receives its power through power cables 35, 36. Diaphragm element 13 is a diaphragm element in the lamella set on the left side 3, which is movably disposed on a bracing members 4 and 6 and bracing members 5 and 7 (not shown in FIG. 5) arranged below them. Lamella set 3 is also displaceable in the direction of arrow 34, and the range of displacement is delimited by external stops 37, 38, and by the rods 18 and 20. Lamella sets 2 and 3 are moved by means of a handwheel 39, with which the lamella sets 2 and 3 can be moved towards and away from each other symmetrically about a center line. Alternatively, the lamella sets 2 and 3 can be driven jointly or separately by means of one or two drive units.

FIG. 5 presents a further, three-dimensional view of a drive unit 17. Motor 22 is arranged on a linkage 23 which drives a drive gearwheel 24 through shaft 25. Another gearwheel 26 is also secured to shaft 25, and cooperates with gearwheel 27. Gearwheel 27 in turn acts on a rotary potentiometer 28 through a shaft 43. The rotary potentiometer 28 passes an analog value to a control unit (not shown), which emulates the position of lamella 13 in the contour collimator.

A resolver can also be disposed instead of rotary potentiometer 28. Such a device emits a preset number of pulses for each revolution, thus passing a digital indication of the lamella position value to the controlling device.

FIG. 6 shows an enlarged illustration of the bottom guide of diaphragm element 14. While diaphragm element 14 is supported on surface 29', contact surfaces 40, 41 and 42 serve for guidance and combine with surface 29' to form a fixed bearing.

Guide plate 50, which is illustrated in FIG. 7, clearly shows the specialized shape of notches 51, 52 and their respectively opposed pins 53, 54. This neat arrangement of notches 51, 52, which also serve as support bearings, and pins 53, 54, which also serve as loose bedding, allows for highly precise positioning of the diaphragm elements. The guide plate is manufactured by wire EDM. This process is inexpensive, fast, and above all extremely accurate.

The principle of the invention is not limited to the embodiment that has been described up to this point. It may be implemented in many different ways. Therefore, the embodiment in FIG. 8 is to be understood as purely exemplary in nature, wherein guide plate 60 is furnished with round notches 61, 62. These round notches 61, 62 serve as support bearings and cooperate with the opposing grooves 63, 64, which serve as a loose bedding.

The section in FIG. 9 illustrates more clearly the way in which a diaphragm element 65 is arranged between a support bearing 61 and a loose bedding 64. Accordingly, diaphragm element 65 displays a rounded extension 67 at one end 66 and a spring extension 69 at the other end 68. The rounded extension 67 is supported in rounded notch 61 and on this side it engages with the drive unit (not shown). Spring extension 69 is seated in groove 64, which is larger than the extension to compensate for longitudinal deviations. This embodiment can also be manufactured easily by wire EDM.

What is claimed is:

1. A contour collimator for radiation therapy comprising a plurality of diaphragm elements having front and back sides and a first and a second terminal portions that are opposite to each other, wherein the diaphragm elements are arranged movably with respect to each other, such movement being powered by a drive unit for each diaphragm element, and wherein each diaphragm element is supported only on the first terminal portion that is positioned near the respective drive unit.

2. The contour collimator according to claim 1, wherein the first terminal portion of each diaphragm element is furnished with a toothed rack that operates in conjunction with the respective drive unit.

3. The contour collimator according to claim 2, further comprising a guide for the diaphragm elements that is disposed directly adjacent to the drive unit.

4. The contour collimator according to claim 3 further comprising a loose bedding that is provided for each diaphragm element on the second terminal portion of diaphragm element opposite to the respective drive unit.

5. The contour collimator according to claim 3, wherein the first terminal portion of at least one diaphragm element near the drive unit in the direction of movement of the diaphragm element is longer than the second terminal portion.

6. The contour collimator according to claim 2, wherein the drive unit comprises a gear wheel driven perpendicularly to the direction of movement of the diaphragms, and wherein said gear wheel is driven over the toothed rack on the first terminal portion of the diaphragm element to translate the diaphragm element.

7. The contour collimator according to claim 1, wherein at least two diaphragm elements are arranged with separation therebetween, opposite and slightly offset relative to one another, and movably towards one another in more than half the distance of separation.

8. The contour collimator according to claim 1, wherein the longitudinal axes of at least two diaphragm elements, which extend from the respective drive units to respective sides opposite to said drive units, form an angle so that the diaphragm elements are arranged in a fan formation.

9. The contour collimator according to claim 1, wherein at least two diaphragm elements form a diaphragm group which is arranged movably in the direction of movement of the diaphragm elements in addition to the movement of individual diaphragm elements.

10. The contour collimator according to claim 9, wherein two diaphragm groups are arranged opposite one another in the direction of movement of the diaphragm elements and movably towards one another on guide rails.

11. The contour collimator according to claim 1, wherein the drive unit is equipped with a rotary potentiometer to record the position of the diaphragms.

12. The contour collimator according to claim 1, wherein the drive units are arranged parallel to each other.

* * * * *

UNITED STATES PATENT AND TRADEMARK OFFICE
CERTIFICATE OF CORRECTION

PATENT NO.     : 6,711,237 B1
DATED          : March 23, 2004
INVENTOR(S)    : Schlegel et al.

It is certified that error appears in the above-identified patent and that said Letters Patent is hereby corrected as shown below:

Column 4,
Line 38, "a bracing members" should be -- bracing members --.

Signed and Sealed this

Fourteenth Day of December, 2004

JON W. DUDAS
*Director of the United States Patent and Trademark Office*